US011273072B2

(12) United States Patent
Price et al.

(10) Patent No.: US 11,273,072 B2
(45) Date of Patent: Mar. 15, 2022

(54) SUPRACHOROIDAL INJECTION DEVICE

(71) Applicant: Gyroscope Therapeutics Limited, London (GB)

(72) Inventors: Daniel W. Price, Loveland, OH (US); Brendan J. Oberkircher, Cincinnati, OH (US); Daniel J. Prenger, Loveland, OH (US); Geoffrey King, Cincinnati, OH (US); Isaac J. Khan, Bridgewater, NJ (US); Michael F. Keane, Downington, PA (US)

(73) Assignee: Gyroscope Therapeutics Limited, London (GB)

( * ) Notice: Subject to any disclaimer, the term of this patent is extended or adjusted under 35 U.S.C. 154(b) by 1101 days.

(21) Appl. No.: 15/865,533

(22) Filed: Jan. 9, 2018

(65) Prior Publication Data

US 2018/0200108 A1    Jul. 19, 2018

Related U.S. Application Data

(60) Provisional application No. 62/445,866, filed on Jan. 13, 2017.

(51) Int. Cl.
*A61F 9/007* (2006.01)
*A61F 9/00* (2006.01)
*A61M 5/46* (2006.01)

(52) U.S. Cl.
CPC ........ *A61F 9/00736* (2013.01); *A61F 9/0008* (2013.01); *A61F 9/0017* (2013.01);
(Continued)

(58) Field of Classification Search
CPC .. A61F 9/00736; A61F 9/0008; A61F 9/0017; A61F 9/00781; A61F 9/007;
(Continued)

(56) References Cited

U.S. PATENT DOCUMENTS 3,738,359 A  * 6/1973 Lindquist ............... A61B 46/23
                                                       128/852
5,409,457 A    4/1995 del Cerro et al.
(Continued)

FOREIGN PATENT DOCUMENTS

CN        103327939 A      9/2013
WO    WO 2015/187629 A1   12/2015
WO    WO 2017/042584 A1    3/2017

OTHER PUBLICATIONS

Kang, Se Woong, et al. "A new instrument for drainage or injection of fluid within subretinal space." *Retina* 23.5 (2003): 661-666.
(Continued)

*Primary Examiner* — Bhisma Mehta
*Assistant Examiner* — Neeraja Gollamudi
(74) *Attorney, Agent, or Firm* — Frost Brown Todd LLC

(57) ABSTRACT

An apparatus includes a body, a cannula, a conduit, and a magnetic element. The cannula extends distally from the body. The cannula is flexible and has a distal end. The cannula defines a lumen distally terminating at the distal end. The cannula is sized and configured to pass between a sclera layer and a choroid layer in a human eye. The conduit is in fluid communication with the lumen. The magnetic element is positioned in the body.

10 Claims, 9 Drawing Sheets

(52) U.S. Cl.
CPC ............ *A61F 9/00781* (2013.01); *A61M 5/46* (2013.01); *A61M 2210/0612* (2013.01)

(58) Field of Classification Search
CPC ............ A61M 5/46; A61M 2210/0612; A61M 25/0127; A61M 25/0158; A61M 2205/0272; A61M 2205/3515; A61M 31/00

See application file for complete search history.

(56) References Cited

U.S. PATENT DOCUMENTS

| | | | |
|---|---|---|---|
| 5,860,986 | A | 1/1999 | Reich et al. |
| 5,964,740 | A | 10/1999 | Ouchi |
| 6,143,004 | A | 11/2000 | Davis et al. |
| 6,162,197 | A | 12/2000 | Mohammad |
| 6,190,353 | B1 | 2/2001 | Makower et al. |
| 6,283,951 | B1 | 9/2001 | Flaherty et al. |
| 6,299,603 | B1 | 10/2001 | Hecker et al. |
| 6,368,315 | B1 | 4/2002 | Gillis et al. |
| 6,413,245 | B1 | 7/2002 | Yaacobi et al. |
| 6,761,724 | B1 | 7/2004 | Zrenner et al. |
| 6,824,532 | B2 | 11/2004 | Gillis et al. |
| 7,189,245 | B2 | 3/2007 | Kaplan |
| 7,207,980 | B2 | 4/2007 | Christian et al. |
| 7,381,404 | B2 | 6/2008 | Schwartz et al. |
| 7,413,734 | B2 | 8/2008 | Mistry et al. |
| 7,914,803 | B2 | 3/2011 | Chowhan et al. |
| 7,918,814 | B2 | 4/2011 | Prausnitz et al. |
| 8,172,830 | B2 | 5/2012 | Christian et al. |
| 8,197,435 | B2 | 6/2012 | Prausnitz et al. |
| 8,298,521 | B2 | 10/2012 | Schwartz et al. |
| 8,425,473 | B2 | 4/2013 | Ho et al. |
| 8,569,272 | B2 | 10/2013 | Lyons et al. |
| 8,636,713 | B2 * | 1/2014 | Prausnitz ............... A61P 27/06 604/521 |
| 8,808,225 | B2 | 8/2014 | Prausnitz et al. |
| 9,314,425 | B2 | 4/2016 | Whitcup |
| 9,486,357 | B2 | 11/2016 | Peyman |
| 9,788,995 | B2 | 10/2017 | Prausnitz et al. |
| 9,956,114 | B2 | 5/2018 | Andino et al. |
| 10,076,526 | B2 | 9/2018 | Shiah et al. |
| 2002/0133184 | A1 | 9/2002 | LoRusso |
| 2002/0143302 | A1 | 10/2002 | Hinchliffe et al. |
| 2004/0039253 | A1 | 2/2004 | Peyman et al. |
| 2004/0138562 | A1 | 7/2004 | Makower et al. |
| 2004/0199130 | A1 * | 10/2004 | Chornenky ............ A61K 31/205 604/289 |
| 2005/0143363 | A1 | 6/2005 | de Juan et al. |
| 2005/0266047 | A1 | 12/2005 | Tu et al. |
| 2006/0025720 | A1 | 2/2006 | Sawa et al. |
| 2006/0047250 | A1 | 3/2006 | Hickingbotham et al. |
| 2006/0293647 | A1 | 12/2006 | McRae et al. |
| 2007/0202186 | A1 | 8/2007 | Yamamoto et al. |
| 2008/0004596 | A1 | 1/2008 | Yun et al. |
| 2008/0058704 | A1 | 3/2008 | Hee et al. |
| 2008/0161845 | A1 | 7/2008 | Murakami et al. |
| 2008/0281292 | A1 | 11/2008 | Hickingbotham et al. |
| 2010/0004499 | A1 | 1/2010 | Brigatti et al. |
| 2010/0042118 | A1 | 2/2010 | Garrison et al. |
| 2010/0173866 | A1 | 7/2010 | Hee et al. |
| 2010/0305514 | A1 | 12/2010 | Valenti et al. |
| 2011/0207987 | A1 | 8/2011 | DiCarlo et al. |
| 2012/0071832 | A1 | 3/2012 | Bunch |
| 2012/0191064 | A1 * | 7/2012 | Conston ............... A61F 9/00727 604/506 |
| 2012/0271272 | A1 * | 10/2012 | Hammack ............... A61M 5/46 604/500 |
| 2012/0323220 | A1 | 12/2012 | Mackay, II et al. |
| 2013/0103026 | A1 | 4/2013 | Kleshinski et al. |
| 2013/0211379 | A1 | 8/2013 | Clair et al. |
| 2013/0216623 | A1 | 8/2013 | Yamamoto et al. |
| 2013/0245600 | A1 | 9/2013 | Yamamoto et al. |
| 2014/0121641 | A1 | 5/2014 | Fischell et al. |
| 2015/0209180 | A1 | 7/2015 | Prausnitz et al. |
| 2015/0223977 | A1 * | 8/2015 | Oberkircher ............ A61M 5/158 604/521 |
| 2015/0258120 | A1 | 9/2015 | Zarnitsyn |
| 2015/0351958 | A1 | 12/2015 | Contiliano et al. |
| 2015/0351959 | A1 | 12/2015 | Clem et al. |
| 2016/0074211 | A1 | 3/2016 | Ko et al. |
| 2016/0074212 | A1 | 3/2016 | Price et al. |
| 2016/0074217 | A1 | 3/2016 | Price et al. |
| 2016/0081849 | A1 | 3/2016 | Tsai et al. |
| 2016/0106587 | A1 * | 4/2016 | Jarrett ................. A61F 9/0017 604/506 |
| 2016/0143776 | A1 * | 5/2016 | Rotenstreich ....... A61F 9/00836 604/21 |
| 2016/0228359 | A1 | 8/2016 | Whitcup |
| 2017/0095369 | A1 | 4/2017 | Andino et al. |
| 2017/0290702 | A1 | 10/2017 | Yamamoto et al. |
| 2017/0333416 | A1 | 11/2017 | Zarnitsyn et al. |
| 2017/0340560 | A1 | 11/2017 | Yamamoto et al. |
| 2017/0360605 | A1 | 12/2017 | Oberkircher et al. |
| 2017/0360606 | A1 | 12/2017 | Price et al. |
| 2018/0028356 | A1 | 2/2018 | Murata |
| 2018/0028357 | A1 | 2/2018 | Prausnitz et al. |
| 2018/0042765 | A1 | 2/2018 | Noronha et al. |
| 2018/0042767 | A1 | 2/2018 | Andino et al. |

OTHER PUBLICATIONS

Komáromy, András M., et al. "Application of a new subretinal injection device in the dog." *Cell transplantation* 15.6 (2006): 511-519.

Olsen, Timothy W., et al. "Cannulation of the suprachoroidal space: a novel drug delivery methodology to the posterior segment." *American journal of ophthalmology* 142.5 (2006): 777-787.

Patel, S. R., et al. "Intraocular Pharmacokinetics of Suprachoroidal Drug Delivery Administered Using Hollow Microneedles." *Investigative Ophthalmology & Visual Science* 51.13 (2010): 3796-3796.

Patel, S., et al. "Suprachoroidal Drug Delivery Using Microneedles." *Investigative Ophthalmology & Visual Science* 49.13 (2008): 5006-5006.

Patel, Samirkumar R., et al. "Suprachoroidal drug delivery to the back of the eye using hollow microneedles." *Pharmaceutical research* 28.1 (2011): 166-176.

Peden, M. C., et al. "Safety Study of Ab-Externo AAV Gene Therapy Delivery to the Subretinal and Suprachoroidal Space Using a 250 Micron Flexible Microcatheter." *Investigative Ophthalmology & Visual Science* 50.13 (2009): 1450-1450.

Schanze, Thomas, et al. "Implantation and testing of subretinal film electrodes in domestic pigs." *Experimental eye research* 82.2 (2006): 332-340.

Soni, M. H., and A. K. Tyagi. "Induction of Choroidal Detachment: A New Surgical Technique for Choroidal Biopsy." *Investigative Ophthalmology & Visual Science* 46.13 (2005): 5438-5438.

Gallab, Mahmoud, et al. "Development of a spherical model with a 3D microchannel: An application to glaucoma surgery." *Micromachines* 10.5 (2019): 297.

Chinese Office Action dated Jun. 5, 2018 for Application No. 201580008275.2, 8 pages.

Chinese Office Action dated Feb. 14, 2019 for Application No. 201580008275.2, 6 pages.

European Communication dated Mar. 7, 2019 for Application No. 15708368.4, 6 pages.

European Communication dated May 19, 2020 for Application No. 15708368.4, 4 pages.

Extended European Search Report dated Mar. 3, 2021, for Application No. 20200019.6, 9 pages.

International Search Report and Written Opinion dated Aug. 27, 2015, for International Application No. PCT/US2015/015362, 14 pages.

International Search Report and Written Opinion dated Jun. 7, 2017 for International Application No. PCT/US2017/021508, 12 pages.

International Preliminary Report on Patentability dated Sep. 11, 2018 for International Application No. PCT/US2017/021508, 8 pages.

(56) References Cited

OTHER PUBLICATIONS

Japanese Office Action dated Nov. 7, 2018 for Application No. 2016-552291, 3 pages.
Japanese Office Action dated Aug. 11, 2020 for Application No. 2019-111845, 6 pages.
U.S. Appl. No. 61/938,956, filed Feb. 12, 2014.
U.S. Appl. No. 62/049,056, filed Sep. 11, 2014.
U.S. Appl. No. 62/049,089, filed Sep. 11, 2014.
U.S. Appl. No. 62/049,100, filed Sep. 11, 2014.
U.S. Appl. No. 62/049,128, filed Sep. 11, 2014.
U.S. Appl. No. 62/104,295, filed Jan. 16, 2015.
U.S. Appl. No. 62/305,767, filed Mar. 9, 2016.

* cited by examiner

SUPRACHOROIDAL INJECTION DEVICE

PRIORITY

This application claims priority to U.S. Provisional Patent App. No. 62/445,866, entitled "Suprachoroidal Injection Device," filed Jan. 13, 2017, the disclosure of which is incorporated by reference herein.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. In some instances, it may be desirable to inject a fluid into the suprachroidal space, between the choroid layer and the sclera. By way of example only, such an injected fluid may include a drug, a viscoelastic to treat retinal detachment, and/or various other kinds of substances to address various kinds of conditions.

Some procedures to inject a fluid into the suprachoroidal space may include the use of a transscleral external needle with a depth control feature that provides a fixed exposed distance of needle penetration into the sclera. This approach may not provide sufficient precision to accommodate variations in patient anatomy, since sclera thickness may vary from patient to patient. In patients with a relatively thin sclera, the needle may penetrate the choroid, and in some cases even penetrate the retina, which may produce an undesirable result. In patients with a relatively thick sclera, the needle may fail to reach the suprachoroidal space, which may render the treatment completely ineffective.

Some other procedures to inject a fluid into the suprachoroidal space may include the use of a rigid steel cannula to enter the suprachoroidal space through a sclerotomy. This approach may be relatively technique sensitive with respect to the angle and depth of entry, such that it may be undesirably too easy to inadvertently penetrate the choroid and retina with the rigid steel cannula.

It may therefore be desirable to provide a device that enables the delivery of fluid into the suprachoroidal space with substantial precision and without substantial risk of inadvertent penetration of the choroid and retina.

While a variety of devices and methods have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
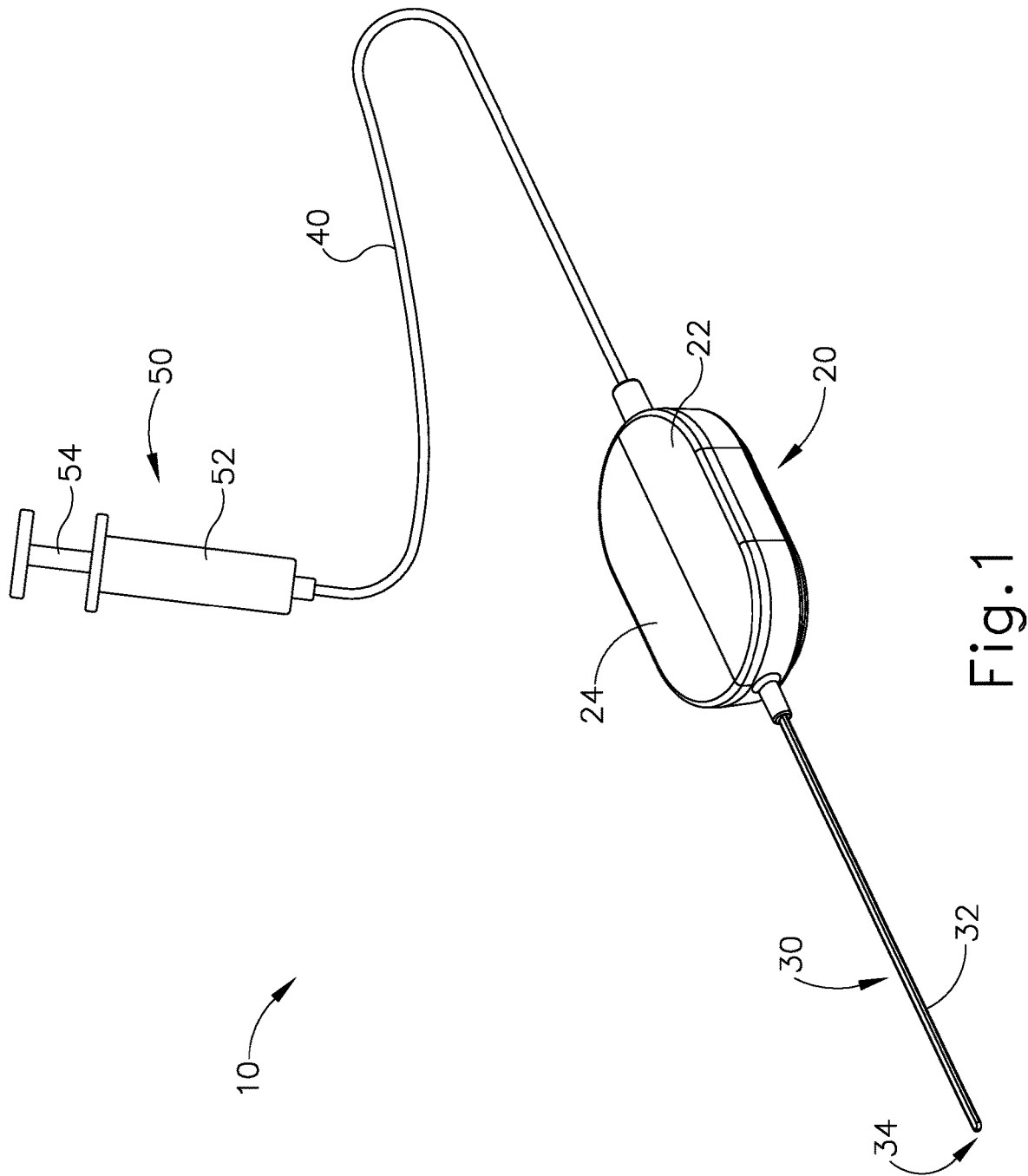
FIG. 1 depicts a perspective view of an exemplary system for delivery of fluid to the suprachoroidal space.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary System for Administration of Fluid to Suprachoroidal Space

FIG. 1 shows an exemplary system (10) that is configured for use in a procedure to deliver fluid to the suprachoroidal space in an eye of a patient. System (10) of this example comprises a body (20), a flexible cannula (30) extending distally from body (20), a flexible conduit (40) extending proximally from body (20), and a syringe (50) that is also coupled with flexible conduit (40). Syringe (50) of the present example has a conventional construction formed by a barrel (52) and a plunger (54). Barrel (52) may contain any suitable fluid, including but not limited to a viscoelastic to treat retinal detachment, and/or various other kinds of substances to address various kinds of conditions. These substances could include a drug in the form of an aqueous or semi-aqueous solution containing one or more of the following: small molecules (e.g., steroid, etc.), large molecules (e.g., monoclonal antibody, etc.), a cell or gene therapy, regenerative medicine product, peptides, proteins, antibodies, genes (and their carriers), glycoproteins, lipoproteins, cells, lysosomes, nanoparticles, excipients (e.g., solubilizers, detergents, antioxidants, etc.), one or more organic chemicals (e.g., in relatively low percentages), and/or any other suitable substance(s) as will be apparent to those of ordinary skill in the art in view of the teachings herein. An operator may actuate plunger (54) to drive the fluid from barrel (52) and into flexible conduit (40). Flexible conduit (40) may comprise any suitable conventional catheter or other tubing, etc.

While syringe (50) is used to provide manual operation of fluid delivery in the present example, some other versions may provide automated fluid delivery. By way of example only, fluid delivery may be automated in accordance with at least some of the teachings of U.S. Pub. No. 2017/0360606, entitled "Injection Device for Subretinal Delivery of Therapeutic Agent," published Dec. 21, 2017, the disclosure of which is incorporated by reference herein. As another merely illustrative example, a fluid source may be integrated into body (20), with manual or automated delivery being provided via one or more components that are also integral with body (20). Other various ways in which fluid delivery may be automated or provided manually will be apparent to those of ordinary skill in the art in view of the teachings herein.

Figure 2:
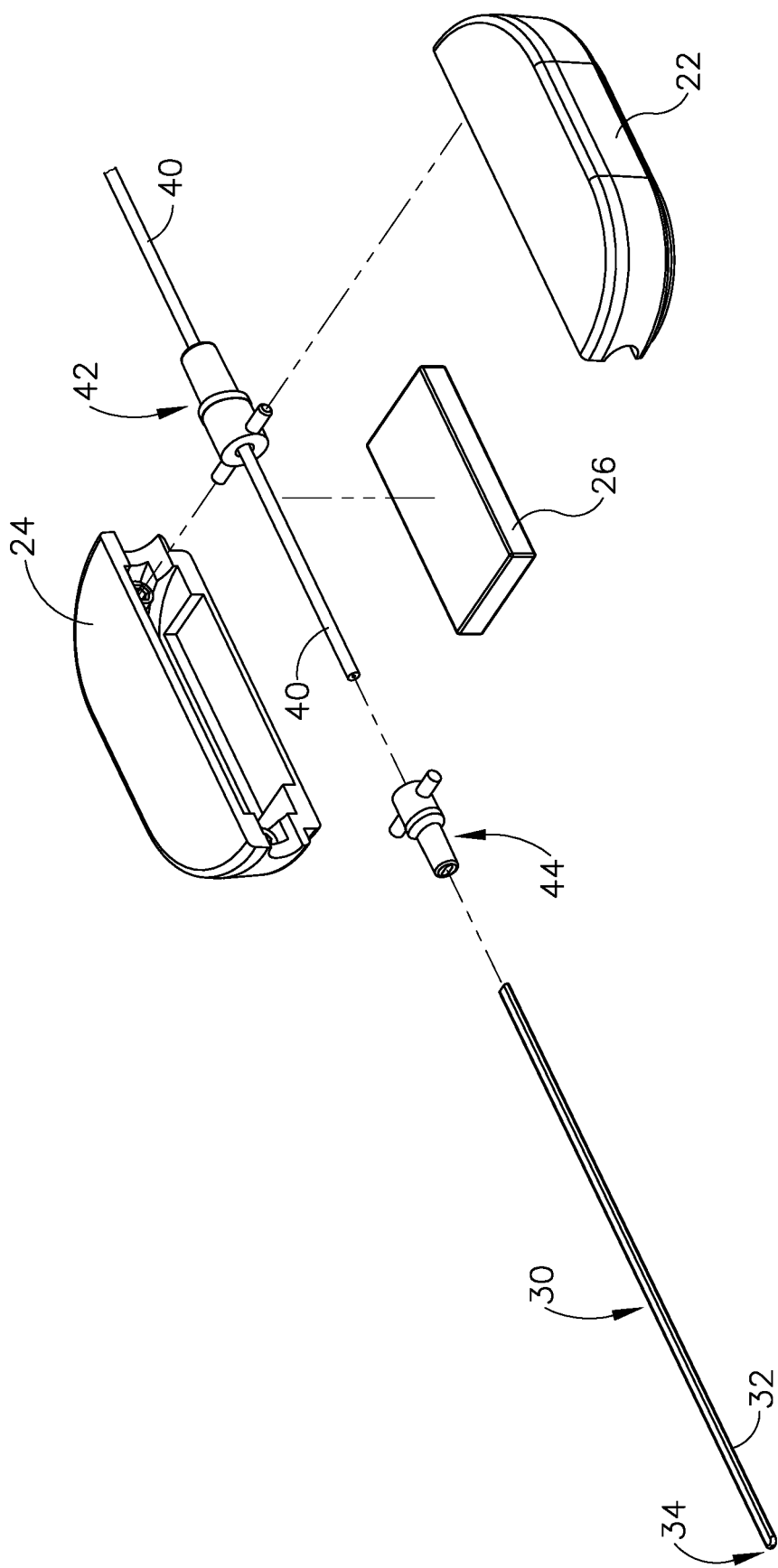
FIG. 2 depicts an exploded view of a fluid delivery device of the system of FIG. 1.
Figure 3:
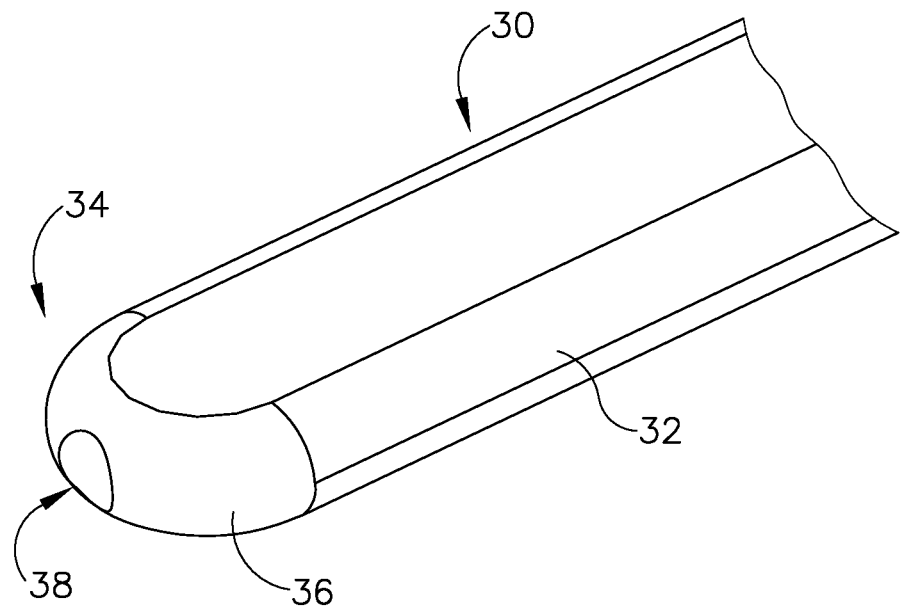
FIG. 3 depicts a perspective view of a distal end of a cannula of the device of FIG. 2.
Figure 4:
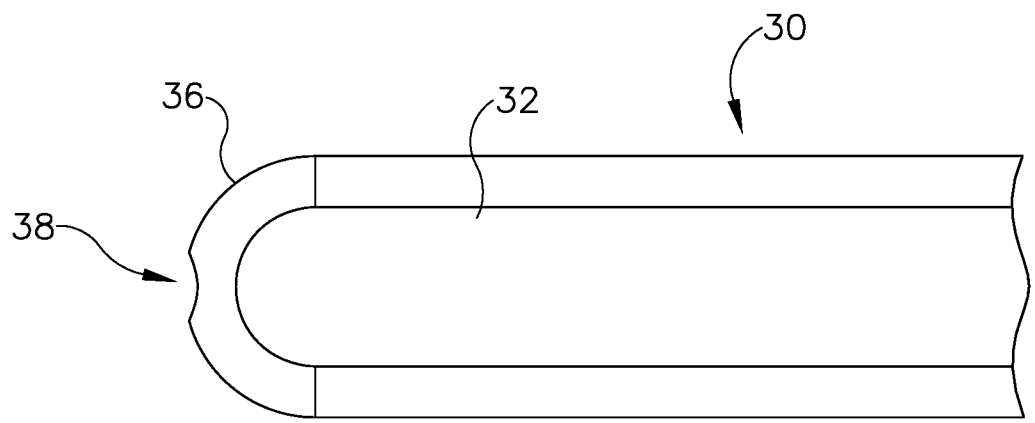
FIG. 4 depicts a top plan view of the distal end of the cannula of FIG. 3.
Figure 5:
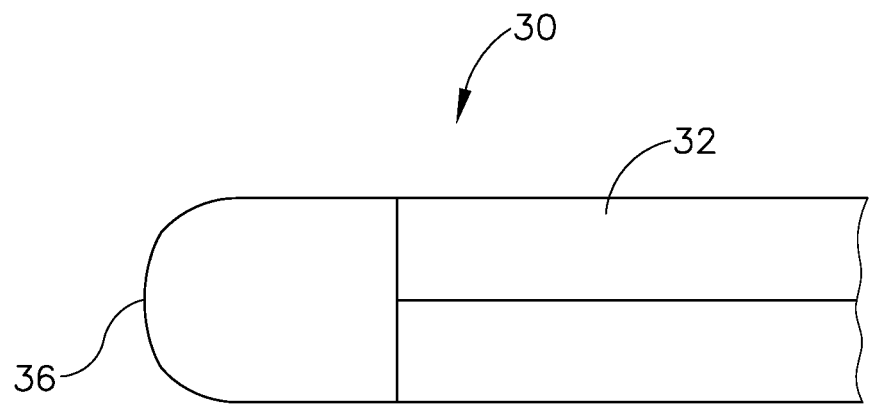
FIG. 5 depicts a side elevational view of the distal end of the cannula of FIG. 3.

As shown in FIGS. 1-2, body (20) comprises a pair of halves (22, 24) that are joined together laterally to form a generally flat oval shape. Alternatively, body (20) may have any other suitable construction and configuration. As also shown in FIG. 2, body (20) contains a permanent magnet block (26). As will be described in greater detail below, permanent magnet block (26) is configured to interact with a magnetic pad (60) to thereby removably secure the position of body (20) relative to a patient. As also shown in FIG. 2, a proximal strain relief assembly (42) is secured at the proximal end of body (20) while a distal strain relief assembly (44) is secured at the distal end of body (20). Conduit (40) is secured to body (20) at proximal strain relief assembly (42), such that proximal strain relief assembly (42) provides strain relief at the interface of conduit (40) and body (20). Cannula (30) is secured to body (20) at distal strain relief assembly (44), such that distal strain relief assembly (44) provides strain relief at the interface of cannula (30) and body (20). Various suitable components and configurations that may be used to form strain relief assemblies (42, 44) will be apparent to those of ordinary skill in the art in view of the teachings herein.

Figure 6:
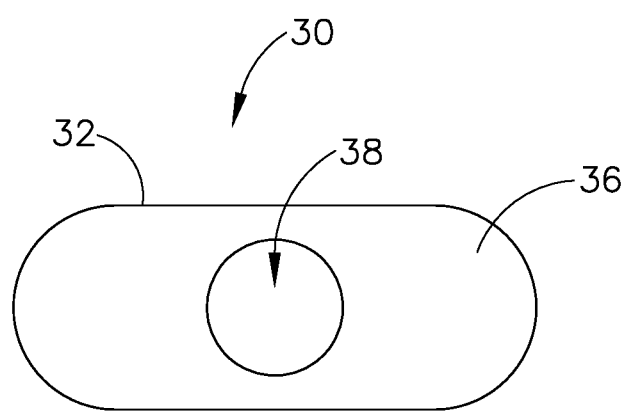
FIG. 6 depicts an end view of the distal end of the cannula of FIG. 3.

FIGS. 3-6 show cannula (30) in greater detail. As shown, cannula (30) of the present example comprises an elongate body (32) with a distal end (34) having a rounded surface (36). A lumen (38) is formed through body (32) and extends along the full length of body (32), such that lumen (38) distally terminates at distal end (34). Lumen (38) is in fluid communication with conduit (40) such that fluid from syringe (50) may be communicated through lumen (38) and out of distal end (34) via conduit (40). Body (32) of the present example has a flattened configuration providing a generally oval-shaped (or rounded-rectangle-shaped) cross-sectional profile as best seen in FIG. 6. This cross-sectional profile, along with rounded surface (36), may enable cannula (30) to atraumatically traverse the suprachoroidal space. Moreover, the oval-shaped (or rounded-rectangle-shaped) cross-sectional profile may prevent cannula (30) from inadvertently twisting or rotating about the longitudinal axis of body (32) as cannula (30) traverses the suprachoroidal space.

By way of example only, cannula (30) may be formed of a flexible material such as Polyether block amide (PEBA), which may be manufactured under the trade name PEBAX. Of course, any other suitable material or combination of materials may be used. Also in the present example, cannula (30) has a cross-sectional profile dimension of approximately 2.0 mm by 0.8 mm, with a length of approximately 80 mm. Alternatively, any other suitable dimensions may be used. Cannula (30) of the present example is flexible enough to conform to specific structures and contours of the patient's eye, yet cannula (30) has sufficient column strength to permit advancement of cannula (30) between the sclera and choroid of patient's eye without buckling. By way of example only, cannula (30) may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein. Also in some versions, cannula (30) includes a flexible polymer tube (not shown) disposed in lumen (38). Such an internal tube may provide additional column strength and/or other properties to cannula (30).

II. Exemplary Procedure for Delivery of Fluid to Suprachoroidal Space

Figure 7:
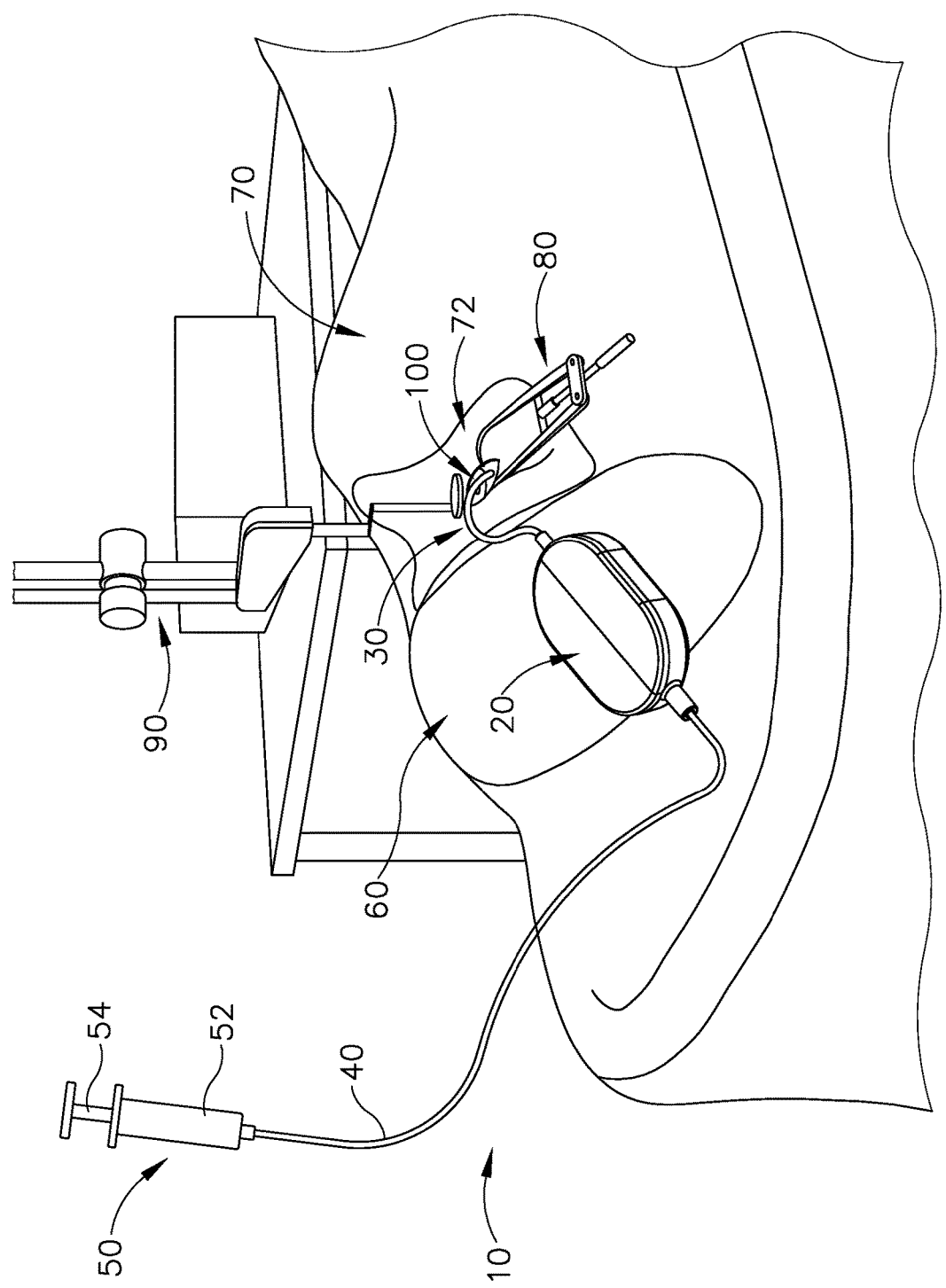
FIG. 7 depicts a perspective view of components of the system of FIG. 1 mounted near a patient.

FIG. 7 shows components of system (10) positioned in relation to a patient during a fluid delivery procedure. In this example, a drape (70) is disposed over the patient, with an opening (72) formed in drape (70) near the patient's eye (100). A speculum (80) is used to keep the eye (100) open. A fixture (90) is positioned adjacent to the eye (100). Fixture (90) may be used to secure instrumentation, such as a viewing scope, relative to the patient. Magnetic pad (60) is adhered to drape (70) near the opening (72) adjacent to the eye (100). Body (20) is placed on magnetic pad (60), and is removably secured thereto via magnetic attraction. For instance, magnetic pad (60) may include one or more magnets or other ferrous elements that provide magnetic attraction for permanent magnet block (26). By way of further example only, magnetic pad (60) may be constructed and operable in accordance with at least some of the teachings of U.S. Pub. No. 2017/0360606, the disclosure of which is incorporated by reference herein. Body (20) is oriented on magnetic pad (60) to enable insertion of a flexible cannula (30) of into the eye (100). As shown, cannula (30) is capable of substantially bending laterally, forming a "U" shape, to appropriately enter the eye (100)

while body (20) is mounted on magnetic pad (60). Syringe (50) is coupled with body (20) and cannula (30) via flexible conduit (40), thereby enabling the operator to drive fluid from barrel (52) into the eye (100) via flexible conduit (40) and cannula (30).

Figure 8A:
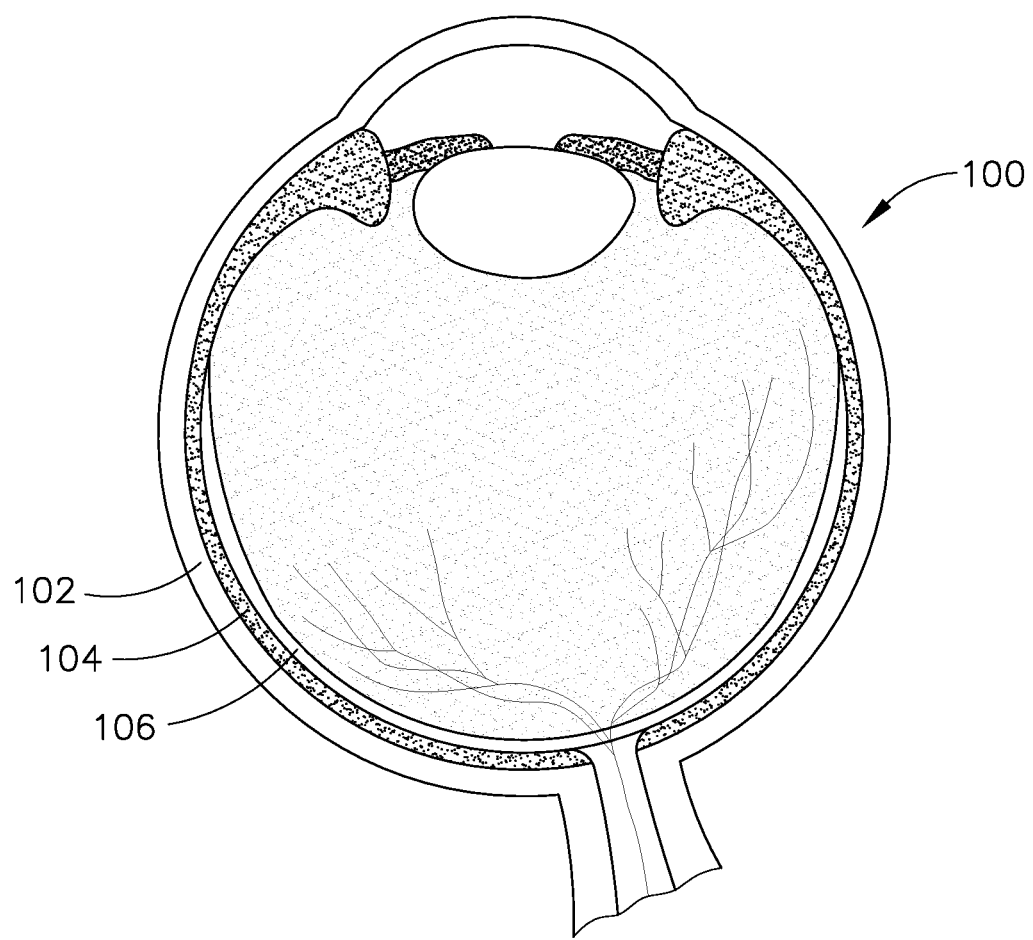
FIG. 8A depicts a cross-sectional view of an eye of a patient.

FIGS. 8A-8D show various steps of a procedure that may be performed to insert cannula (30) into the eye (100) and thereby deliver fluid to the suprachoroidal space. It should be understood that such a procedure may be performed using the arrangement shown in FIG. 7. As shown in FIG. 8A, the sclera (102) is the outermost layer of the eye (100), with the choroid (104) being internal relative to the sclera (102), and with the retina (106) being internal relative to the choroid (104). The suprachoroidal space is defined between the exterior of the choroid (104) and the interior of the sclera (102). As noted above with reference to FIG. 7, the procedure begins with the eye (100) being immobilized, such as by a speculum (80). Fixture (90) is used to position a viewing scope over the eye (100), enhancing visualization for the operator to look into the eye (100).

After speculum (80) and fixture (90) are appropriately positioned, the sclera (102) may be accessed by dissecting the conjunctiva by incising a flap in the conjunctiva and pulling the flap posteriorly. After such a dissection is completed, the exposed surface of the sclera (102) may optionally be blanched using a cautery tool to minimize bleeding. Once conjunctiva dissection is complete, the exposed surface of the sclera (102) may optionally be dried using a WECK-CEL or other suitable absorbent device. A template may then be used to mark the eye (100), as described in U.S. Pub. No. 2015/0223977, entitled "Method and Apparatus for Subretinal Administration of Therapeutic Agent," published Aug. 13, 2015, the disclosure of which is incorporated by reference herein; and/or as described in U.S. Pub. No. 2017/0360605, entitled "Guide Apparatus for Tangential Entry into Suprachoroidal Space," published Dec. 21, 2017, the disclosure of which is incorporated by reference herein.

Figure 8B:
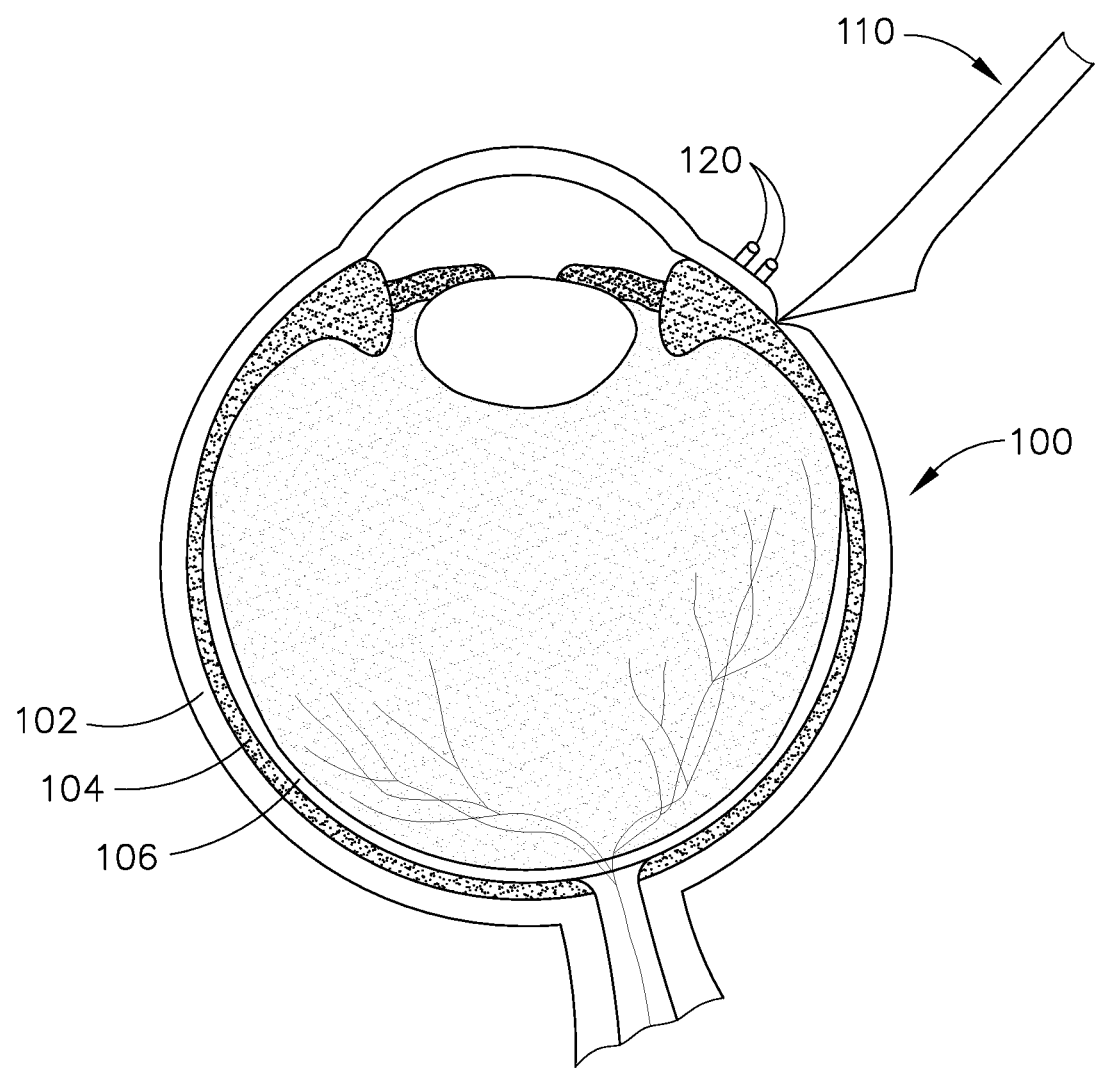
FIG. 8B depicts a cross-sectional view of the eye of FIG. 8A, with a suture loop attached to the eye, and with a sclerotomy being performed.

An operator may then use a visual guide created using the template to attach a suture loop assembly (120), as shown in FIG. 8B, which will serve as a guide for cannula (30) as described in greater detail below. By way of example only, suture loop assembly (120) may be formed in accordance with at least some of the teachings of U.S. Pub. No. 2015/0223977, the disclosure of which is incorporated by reference herein. While the procedure of the present example employs the use of a suture loop assembly (120), alternative kinds of guide structures may be used. By way of example only, such alternative guides may comprise any of the various tacks or other guide devices described in U.S. Pub. No. 2017/0360605, the disclosure of which is incorporated by reference herein. Alternatively, any other suitable kind of guide structure may be used.

In addition to creating suture loop assembly (120), the operator in the present example also uses a visual guide created using the template to perform a sclerotomy, as shown in FIG. 8B, using a conventional scalpel (110) or other suitable cutting instrument. The sclerotomy procedure forms a small incision (130) through the sclera (102) of the eye (100). The sclerotomy is performed with particular care to avoid penetration of the choroid (104). Thus, the sclerotomy procedure provides access to the space between the sclera (102) and the choroid (104). Once the incision (130) is made in the eye (100), a blunt dissection may optionally be performed to locally separate the sclera (102) from the choroid (104). Such a dissection may be performed using a small blunt elongate instrument, as will be apparent to those of ordinary skill in the art in view of the teachings herein.

Figure 8C:
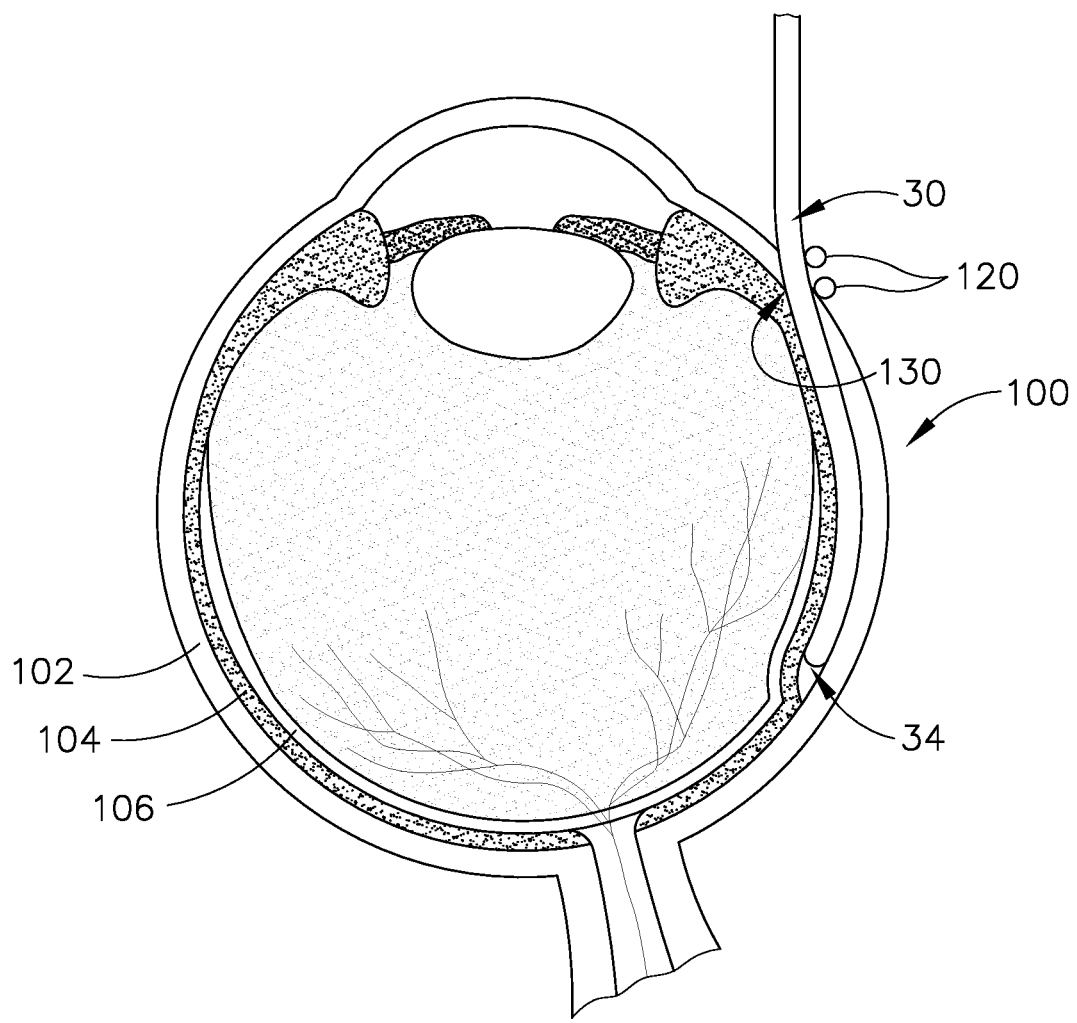
FIG. 8C depicts a cross-sectional view of the eye of FIG. 8A, with the cannula of FIG. 3 being inserted through the sclerotomy opening and in between the sclera and choroid of the eye.

With the sclerotomy procedure performed, the operator then inserts cannula (30) of instrument (10) through incision (130) and into the space between the sclera (102) and the choroid (104). As can be seen in FIG. 8C, cannula (30) is directed through suture loop assembly (120) and into the incision (130). Suture loop assembly (120) may stabilize cannula (30) during insertion. Additionally, suture loop assembly (120) maintains cannula (30) in a generally tangential orientation relative to the incision (130). Such tangential orientation may reduce trauma as cannula (30) is guided through the incision (130). As cannula (30) is inserted into the incision (130) through suture loop assembly (120), an operator may use forceps or other instruments to further guide cannula (30) along an atraumatic path. Of course, use of forceps or other instruments is merely optional, and may be omitted in some examples.

As cannula (30) traverses the space between the choroid (104) and the sclera (102), traveling from the incision (130) to the point where distal end (34) is shown in FIG. 8C, cannula (30) provides some degree of separation between the choroid (104) and the sclera (102) (e.g., like a blunt dissection). During this traversal, cannula (30) substantially conforms to the curvature defined by the inner surface of the sclera (102).

Although not shown, in some examples cannula (30) may include one or more markers on the surface of cannula (30) to indicate various depths of insertion. While merely optional, such markers may be desirable to aid an operator in identifying the proper depth of insertion as cannula (30) is guided along an atraumatic path. For instance, the operator may visually observe the position of such markers in relation to suture loop assembly (120) and/or in relation to the incision (130) in the sclera (102) as an indication of the depth to which cannula (30) is inserted in the eye (100). By way of example only, one such marker may correspond to an approximately 6 mm depth of insertion of cannula (30). Those of ordinary skill in the art will recognize that cannula (30) may be inserted into the eye (100) under direct visualization, such that fiber optics or other special illumination are not necessarily required.

Figure 8D:
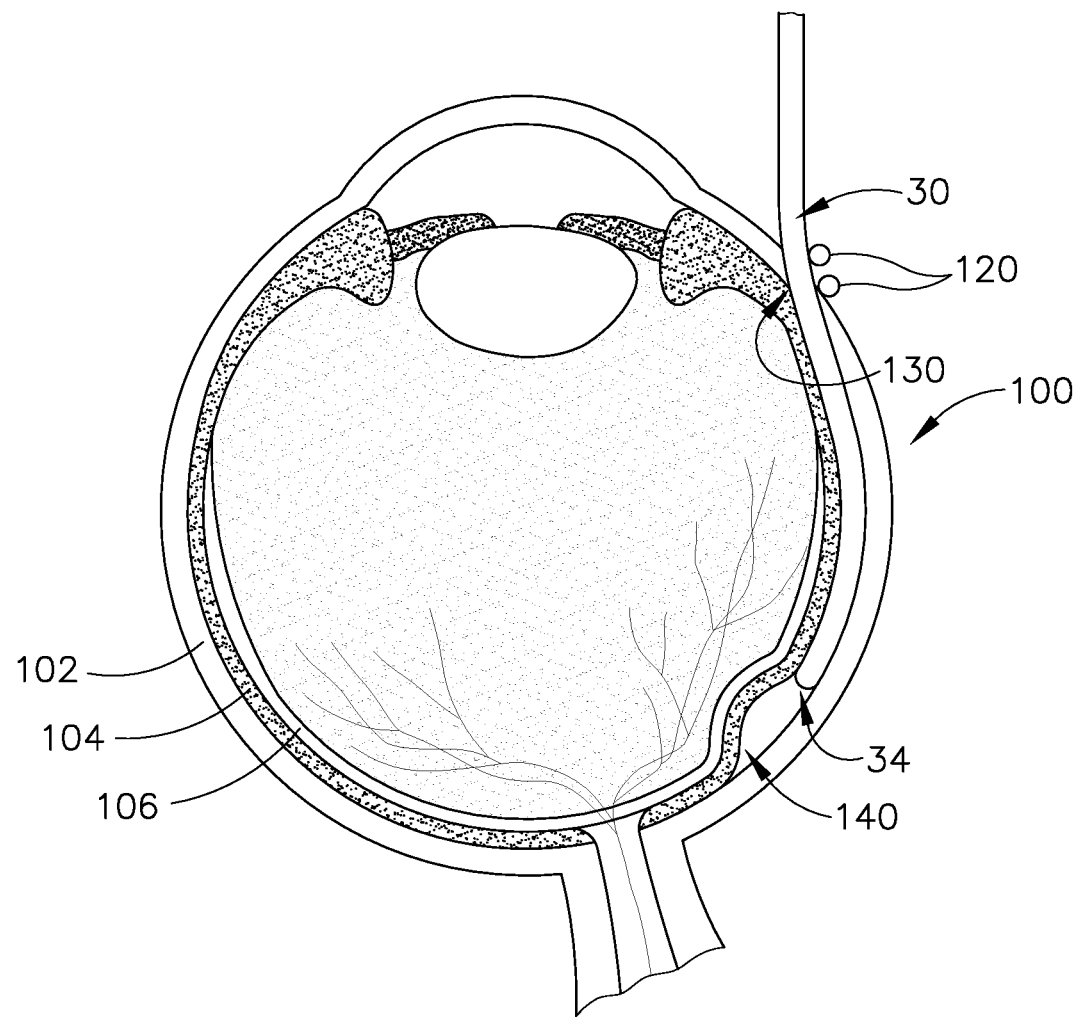
FIG. 8D depicts a cross-sectional view of the eye of FIG. 8A, with the cannula of FIG. 3 delivering fluid to the suprachoroidal space between the sclera and choroid of the eye.

As shown in FIG. 8D, once cannula (30) is inserted into the eye (100) to a point where distal end (34) of cannula (320) is at the appropriate position in the suprachoroidal space (i.e., between the exterior of the choroid (104) and the interior of the sclera (102)), the operator may actuate syringe (50) to thereby drive fluid (140) through conduit (40) and lumen (38), and thereby out through distal end (34) of cannula (30), into the suprachoroidal space. As noted above, fluid (140) may comprise a viscoelastic to treat retinal detachment, and/or various other kinds of substances to address various kinds of conditions. These substances could include a drug in the form of an aqueous or semi-aqueous solution containing one or more of the following: small molecules (e.g., steroid, etc.), large molecules (e.g., monoclonal antibody, etc.), a cell or gene therapy regenerative medicine product, peptides, proteins, antibodies, genes (and their carriers), glycoproteins, lipoproteins, cells, lysosomes, nanoparticles, excipients (e.g., solubilizers, detergents, antioxidants, etc.), one or more organic chemicals (e.g., in relatively low percentages), and/or any other suitable substance(s). Other kinds of substances that may be contained in fluid (140) will be apparent to those of ordinary skill in the art in view of the teachings herein. Syringe (50) may be preloaded with an appropriate volume of fluid (140) such that the operator simply actuates syringe (50) to the fullest extent in order to expel the entire contents of fluid (140) from barrel (52). By way of example only, the volume may range between approximately 25 microliters to approximately 2 milliliters, or more particularly between approximately 100 microliters and approximately 300 microliters. Alternatively, any other suitable volume may be used.

In the present example, the delivery site corresponds to a generally posterior region of the eye (100). Of course, the appropriate position of a delivery site may vary, such that in various procedures the appropriate delivery site may be anterior or posterior to the delivery site shown in FIG. 8D.

Once fluid (140) is delivered to the suprachoroidal space, the operator may withdraw cannula (30) from the eye (100). Suture loop assembly (120) is then removed, and the incision (130) in the sclera (102) is closed using any suitable conventional technique. While FIG. 8D shows delivered fluid (140) as being substantially concentrated in one particular region of the suprachoroidal space, those of ordinary skill in the art will recognize that the delivered fluid (140) may soon be effectively distributed along a larger region of the suprachoroidal space, such that the delivered fluid (140) will not necessarily remain contained in the particular region shown in FIG. 8D.

Those of ordinary skill in the art will recognize that the above-described procedure, and the structural configuration of cannula (30), may provide substantial precision to delivery of fluid (140) to the suprachoroidal space. In addition, the above-described procedure, and the structural configuration of cannula (30), may substantially reduce the risk of inadvertent penetration of the choroid (104) and retina (106) (as compared to conventional techniques/instruments for delivering fluid to the suprachoroidal space). The above-described procedure and system (10) may thus ultimately provide a relatively short learning curve for operators seeking to deliver fluid (140) to the suprachoroidal space of an eye (100) of a patient.

By way of example only, the above-described procedure and system (10) may be used to deliver fluid (140) to the suprachoroidal space of an eye (100) of a patient having retinal detachment, age related macular degeneration, diabetic macular edema, inherited retinal diseases, retinitis pigmentosa, retinal vein occlusion, diabetic retinopathy, posterior uveitis, Stargardt disease, etc. Other suitable scenarios in which it may be desirable to deliver fluid (140) to the suprachoroidal space of an eye (100) of a patient will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) a cannula extending distally from the body, wherein the cannula is flexible, wherein the cannula has a distal end, wherein the cannula defines a lumen distally terminating at the distal end, wherein the cannula is sized and configured to pass between a sclera layer and a choroid layer in a human eye; (c) a conduit in fluid communication with the lumen; and (d) a magnetic element positioned in the body.

Example 2

The apparatus of Example 1, wherein the distal end of the cannula is rounded.

Example 3

The apparatus of any one or more of Examples 1 through 2, wherein the cannula has a pair of opposing flat sides and a pair of opposing rounded sides, wherein the flat sides and the rounded sides together define a cross-sectional perimeter of the cannula.

Example 4

The apparatus of any one or more of Examples 1 through 3, further comprising a fluid source coupled with the conduit, wherein the lumen and the conduit are operable to communicate fluid from the fluid source.

Example 5

The apparatus of Example 4, wherein the fluid source comprises a syringe.

Example 6

The apparatus of any one or more of Examples 4 through 5, wherein the fluid source is spaced away from the body via the conduit.

Example 7

The apparatus of any one or more of Examples 1 through 6, wherein the conduit comprises a flexible tube.

Example 8

The apparatus of any one or more of Examples 1 through 7, wherein the cannula defines a longitudinal axis, wherein the distal end has an opening positioned on the longitudinal axis, wherein the opening is in fluid communication with the lumen.

Example 9

A method of delivering fluid to an eye of a patient, the method comprising: (a) inserting a flexible cannula between a sclera layer and a choroid layer of the eye of the patient, wherein the cannula has an atraumatic distal end defining a distal opening; and (b) dispensing a fluid into a space between the sclera layer and the choroid layer of the eye of the patient via the distal opening of the cannula.

Example 10

The method of Example 9, further comprising forming an incision in the sclera layer, wherein the act of inserting comprises inserting the flexible cannula through the incision.

Example 11

The method of any one or more of Examples 9 through 10, further comprising securing a guide to the eye of the patient, wherein the act of inserting comprises passing the flexible cannula through a portion of the guide.

Example 12

The method of Example 11, wherein the guide comprises a suture loop assembly.

Example 13

The method of any one or more of Examples 9 through 12, wherein the flexible cannula extends distally from an instrument body, wherein the method further comprises securing the instrument body to the patient.

Example 14

The method of Example 13, wherein the body includes a magnetic element, the method further comprising securing a magnetic pad to the patient, wherein the act of securing the instrument body comprises engaging the magnetic element with the magnetic pad.

Example 15

The method of any one or more of Examples 9 through 14, wherein the act of dispensing the fluid comprises actuating a syringe, wherein the syringe is in fluid communication with the distal opening of the cannula.

Example 16

The method of any one or more of Examples 9 through 15, wherein the act of inserting comprises positioning the distal end to a posterior region of the eye of the patient, wherein the act of dispensing comprises dispensing the fluid into the space between the sclera layer and the choroid layer in the posterior region of the eye of the patient.

Example 17

The method of any one or more of Examples 9 through 16, wherein the cannula separates a portion of the choroid layer from an adjacent portion of the sclera layer during the act of inserting.

Example 18

The method of any one or more of Examples 9 through 17, wherein the cannula confirms to a curvature of an inner surface of the choroid layer during the act of inserting.

Example 19

A method of delivering fluid to an eye of a patient, the method comprising: (a) securing a body of an instrument relative to a patient, wherein the instrument includes a flexible cannula extending distally from the body, wherein the flexible cannula has an atraumatic open distal end; (b) forming an incision in the sclera layer of an eye of the patient; (c) inserting the flexible cannula through the incision, thereby positioning distal end of the cannula in a space between the sclera layer and the choroid layer of the eye of the patient, wherein the flexible cannula conforms to a curvature defined by the sclera layer during the act of inserting; and (d) delivering a fluid via the open distal end of the cannula into the space between the sclera layer and the choroid layer of the eye of the patient.

Example 20

The method of Example 19, further comprising securing a magnetic pad relative to the patient, wherein the body of the instrument includes a magnetic element, wherein the act of securing the body of the instrument relative to a patient comprises achieving a magnetic coupling between the magnetic element and the magnetic pad.

IV. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of delivering fluid to an eye of a patient, the method comprising:
   (a) securing an instrument body relative to the patient;
   (b) inserting a flexible cannula between an interior of a sclera layer and an exterior of a choroid layer of the eye of the patient, wherein the flexible cannula has an atraumatic distal end defining a distal opening, the flexible cannula extending distally from the instrument body, the act of inserting the flexible cannula being performed while the instrument body is secured relative to the patient;
   (c) advancing the flexible cannula along a space between the sclera layer and the choroid layer to position the atraumatic distal end in a posterior region of the eye of the patient, the flexible cannula conforming to a curvature of the interior of the sclera layer during the act of advancing, the flexible cannula further separating a portion of the choroid layer from an adjacent portion of the sclera layer during the act of advancing, the act of advancing the flexible cannula being performed while the instrument body is secured relative to the patient; and
   (d) dispensing a fluid into a space between the sclera layer and the choroid layer of the eye of the patient via the distal opening of the flexible cannula, the act of dispensing the fluid being performed while the instrument body is secured relative to the patient.

2. The method of claim 1, further comprising forming an incision in the sclera layer, wherein the act of inserting comprises inserting the flexible cannula through the incision.

3. The method of claim 1, further comprising securing a guide to the eye of the patient, wherein the act of inserting comprises passing the flexible cannula through a portion of the guide.

4. The method of claim 3, wherein the guide comprises a suture loop assembly.

5. The method of claim 1, wherein the act of securing the instrument body relative to the patient comprises securing the instrument body to the patient.

6. The method of claim 5, wherein the body includes a magnetic element, the method further comprising securing a magnetic pad to the patient, wherein the act of securing the instrument body comprises engaging the magnetic element with the magnetic pad.

7. The method of claim 1, wherein the act of dispensing the fluid comprises actuating a syringe, wherein the syringe is in fluid communication with the distal opening of the cannula.

8. The method of claim 1, wherein the act of dispensing comprises dispensing the fluid into the space between the sclera layer and the choroid layer in the posterior region of the eye of the patient.

9. A method of delivering fluid to an eye of a patient, the method comprising:
   (a) securing a body of an instrument to a patient, wherein the instrument includes a flexible cannula extending distally from the body, wherein the flexible cannula has an atraumatic open distal end;
   (b) forming an incision in a sclera layer of an eye of the patient, the incision being formed in an anterior region of the eye of the patient;
   (c) inserting the flexible cannula through the incision, thereby positioning the atraumatic open distal end of the cannula in a space between an interior of the sclera layer and an exterior of a choroid layer at a posterior region of the eye of the patient, wherein the flexible cannula conforms to a curvature defined by the sclera layer during the act of inserting, the act of inserting the flexible cannula being performed while the body is secured to the patient; and
   (d) delivering a fluid via the open distal end of the cannula into the space between the sclera layer and the choroid layer at the posterior region of the eye of the patient, the act of delivering the fluid being performed while the body is secured to the patient.

10. The method of claim 9, further comprising securing a magnetic pad relative to the patient, wherein the body of the instrument includes a magnetic element, wherein the act of securing the body of the instrument relative to a patient comprises achieving a magnetic coupling between the magnetic element and the magnetic pad.

* * * * *